(12) United States Patent
Salmon et al.

(10) Patent No.: US 12,133,955 B2
(45) Date of Patent: Nov. 5, 2024

(54) RESPIRATORY MASK WITH CHEEK SUPPORTS

(71) Applicant: Fisher & Paykel Healthcare Limited, Auckland (NZ)

(72) Inventors: Andrew Paul Maxwell Salmon, Auckland (NZ); Jonathan David Harwood, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/482,338

(22) Filed: Oct. 6, 2023

(65) Prior Publication Data

US 2024/0123174 A1    Apr. 18, 2024

Related U.S. Application Data

(63) Continuation of application No. 17/546,571, filed on Dec. 9, 2021, now Pat. No. 11,813,383, which is a
(Continued)

(51) Int. Cl.
*A61M 16/06* (2006.01)
*A61M 16/08* (2006.01)

(52) U.S. Cl.
CPC ........ *A61M 16/0666* (2013.01); *A61M 16/06* (2013.01); *A61M 16/0605* (2014.02); *A61M 16/0683* (2013.01); *A61M 16/0816* (2013.01); *A61M 16/0875* (2013.01); *A61M 2207/00* (2013.01); *A61M 2210/06* (2013.01); *A61M 2210/0618* (2013.01)

(58) Field of Classification Search
CPC .. A61M 16/00; A61M 16/06; A61M 16/0605; A61M 16/0611; A61M 16/0666; A61M 16/0683; A61M 16/0816; A61M 16/0672; A61M 16/0875; A61M 2210/06; A61M 2210/0618; A61M 2207/00; A61M 2207/10
See application file for complete search history.

(56) References Cited

U.S. PATENT DOCUMENTS

| 853,439 A | 5/1907 | Clark |
| 2,499,650 A | 3/1950 | Kaslow |
(Continued)

FOREIGN PATENT DOCUMENTS

| WO | WO 2003/066145 | 8/2003 |
| WO | WO 2009/109005 | 9/2009 |
(Continued)

*Primary Examiner* — Colin W Stuart
(74) *Attorney, Agent, or Firm* — Knobbe, Martens, Olson & Bear, LLP

(57) ABSTRACT

A respiratory mask can have a frame supporting a sealing arrangement. Various features of the frame and sealing arrangement can improve comfort and reduce the occurrence of pressure sores. The frame can include cheek supports that have a large surface area configured to spread loads over a greater area of the patient's face and therefore reduce the forces applied to the face and the occurrence of point loads. The seal can have a main body that includes a spring with a silicone skin, wherein the spring applies a substantially constant force to the face and/or nares of the patient.

14 Claims, 11 Drawing Sheets

Related U.S. Application Data continuation of application No. 16/601,127, filed on Oct. 14, 2019, now Pat. No. 11,224,711, which is a continuation of application No. 15/135,020, filed on Apr. 21, 2016, now Pat. No. 10,441,736.

(60) Provisional application No. 62/152,348, filed on Apr. 24, 2015.

(56) References Cited

U.S. PATENT DOCUMENTS

| | | | |
|---|---|---|---|
| 3,754,552 A | 8/1973 | King | |
| 4,915,105 A | 4/1990 | Lee | |
| 5,122,052 A * | 6/1992 | Trame | F16F 1/025 |
| | | | 249/176 |
| 5,988,612 A * | 11/1999 | Bertelson | B29C 70/50 |
| | | | 267/148 |
| 6,012,455 A | 1/2000 | Goldstein | |
| 6,119,694 A | 9/2000 | Correa et al. | |
| 7,201,169 B2 | 4/2007 | Wilkie et al. | |
| 7,370,652 B2 | 5/2008 | Matula, Jr. et al. | |
| 7,493,902 B2 | 2/2009 | White et al. | |
| 9,889,267 B2 | 2/2018 | Wells et al. | |
| 10,441,736 B2 | 10/2019 | Salmon et al. | |
| 10,471,228 B2 * | 11/2019 | Scampoli | B29C 45/261 |
| 11,224,711 B2 | 1/2022 | Salmon et al. | |
| 2006/0283461 A1 | 12/2006 | Lubke et al. | |
| 2008/0105264 A1 | 5/2008 | Gunartnam et al. | |
| 2009/0044808 A1 | 2/2009 | Guney et al. | |
| 2010/0000534 A1 | 1/2010 | Kooij et al. | |
| 2010/0258136 A1 | 10/2010 | Doherty et al. | |
| 2010/0307502 A1 | 12/2010 | Rummery et al. | |
| 2012/0132209 A1 | 5/2012 | Rummery et al. | |
| 2012/0157794 A1 | 6/2012 | Goodwin et al. | |
| 2014/0261432 A1 | 9/2014 | Eves et al. | |
| 2014/0366885 A1 | 12/2014 | Haibach et al. | |
| 2015/0217074 A1 | 8/2015 | Wells et al. | |
| 2016/0089261 A1 | 3/2016 | Quinn | |
| 2019/0030274 A1 | 1/2019 | Rashidi et al. | |

FOREIGN PATENT DOCUMENTS

| | | |
|---|---|---|
| WO | WO 2011/062510 | 5/2011 |
| WO | WO 2014/142681 | 9/2014 |

* cited by examiner

RESPIRATORY MASK WITH CHEEK SUPPORTS

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present disclosure generally relates to a respiratory mask. More particularly, the present disclosure relates to a respiratory mask having large cheek supports for stabilizing a sealing arrangement on a patient's face.

Description of the Related Art

Respiratory masks are used to provide respiratory therapies such as but not limited to non-invasive ventilation (NIV), continuous positive air pressure (CPAP) and high flow therapy to patients. They typically comprise a sealing arrangement configured to form an air-tight seal about a patient's nose and/or mouth that is supported by a frame and headgear. In some cases it can be considered desirable to minimize the size of respiratory masks and their components in order to make them less obtrusive on a patient's face. This minimization often results in the frame having small surface areas in the locations that contact a patient's face. These small surface areas that are in contact with the patient's face can become pressure points that may cause damage in the form of pressure sores and/or discomfort to the patient's skin, when a load is applied to the frame by the headgear.

SUMMARY OF THE INVENTION

The present disclosure relates to a respiratory mask which may at least go some way towards improving on the above or that may at least provide the public with a useful choice.

In accordance with at least one of the embodiments described herein a respiratory mask is provided, having a frame comprising a pair of cheek supports and a bridge portion. The cheek supports have a large contact area configured to engage the non-boney regions of a patient's cheeks. The bridge portion extends between the cheek supports and is configured to support a sealing arrangement.

According to a further aspect the frame of the respiratory mask is supported on a patient's face by a headgear system.

According to a further aspect the bridge portion is supported off the patient's lip.

According to a further aspect the bridge portion is configured to support a sealing arrangement.

According to a further aspect the sealing arrangement comprises a pair of nasal prongs configured to sealingly engage with the nares of the patient.

According to a further aspect the cheek supports are semi-rigid and flex laterally.

According to a further aspect the bridge portion further comprises a plenum chamber and a bias flow vent.

According to a further aspect the respiratory mask further comprising a tube housing configured to secure an air supply tube to the frame.

According to a further aspect the tube housing comprises an opening on a first end and a bung on a second end.

According to a further aspect the tube housing can be connected to the frame such that the air supply tube is connected to either of the first or second sides of the plenum chamber.

According to a further aspect the headgear system has a pair of side straps that extend between the cheek supports and a patients face to form a cheek pad.

According to a further aspect the sealing arrangement comprises a pair of nasal prongs.

According to a further aspect the nasal prongs comprise a main body sealing surface and an outlet, wherein the main body comprises an elongate tube having a wall structure formed by a spring covered with silicone skin.

In accordance with at least one of the embodiments described herein a sealing arrangement for a respiratory mask comprising a main body having first and second ends, a sealing surface and an outlet is provided. The main body comprises an elongate tube having a resilient structure formed by a spring covered with a silicone skin, and the sealing surface is supported by the main body.

According to an aspect an air flow path is provided through the center of the spring that forms the main body of the sealing arrangement.

According to a further aspect the sealing arrangement comprises a nasal prong, wherein the sealing surface engages the nares of a patient.

According to a further aspect the sealing arrangement is configured to be supported by a frame that engages a patient's cheeks.

DETAILED DESCRIPTION

Figure 1A:
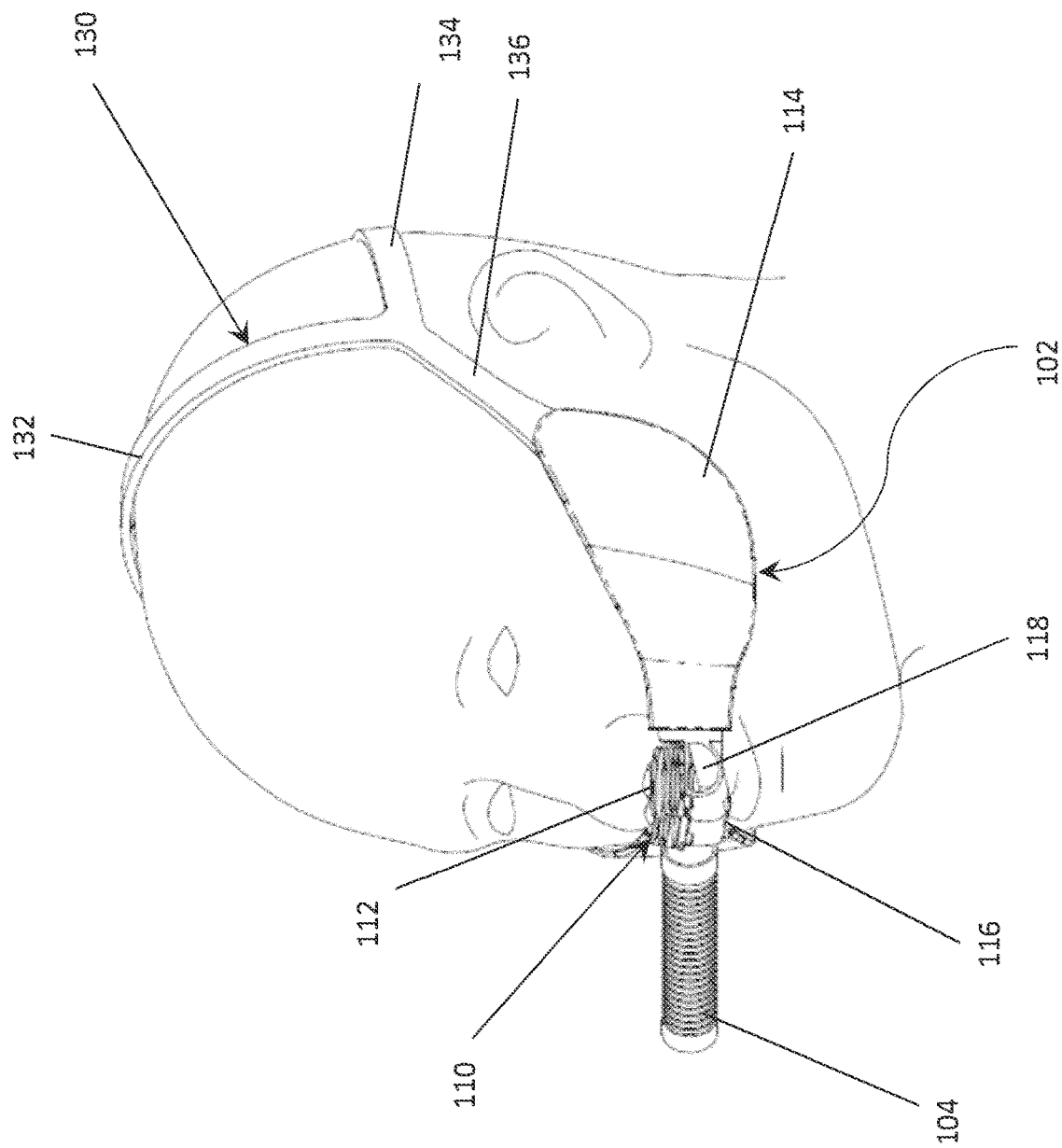
FIG. 1a is a perspective view of the respiratory mask of the present disclosure, worn by a patient.
Figure 1B:
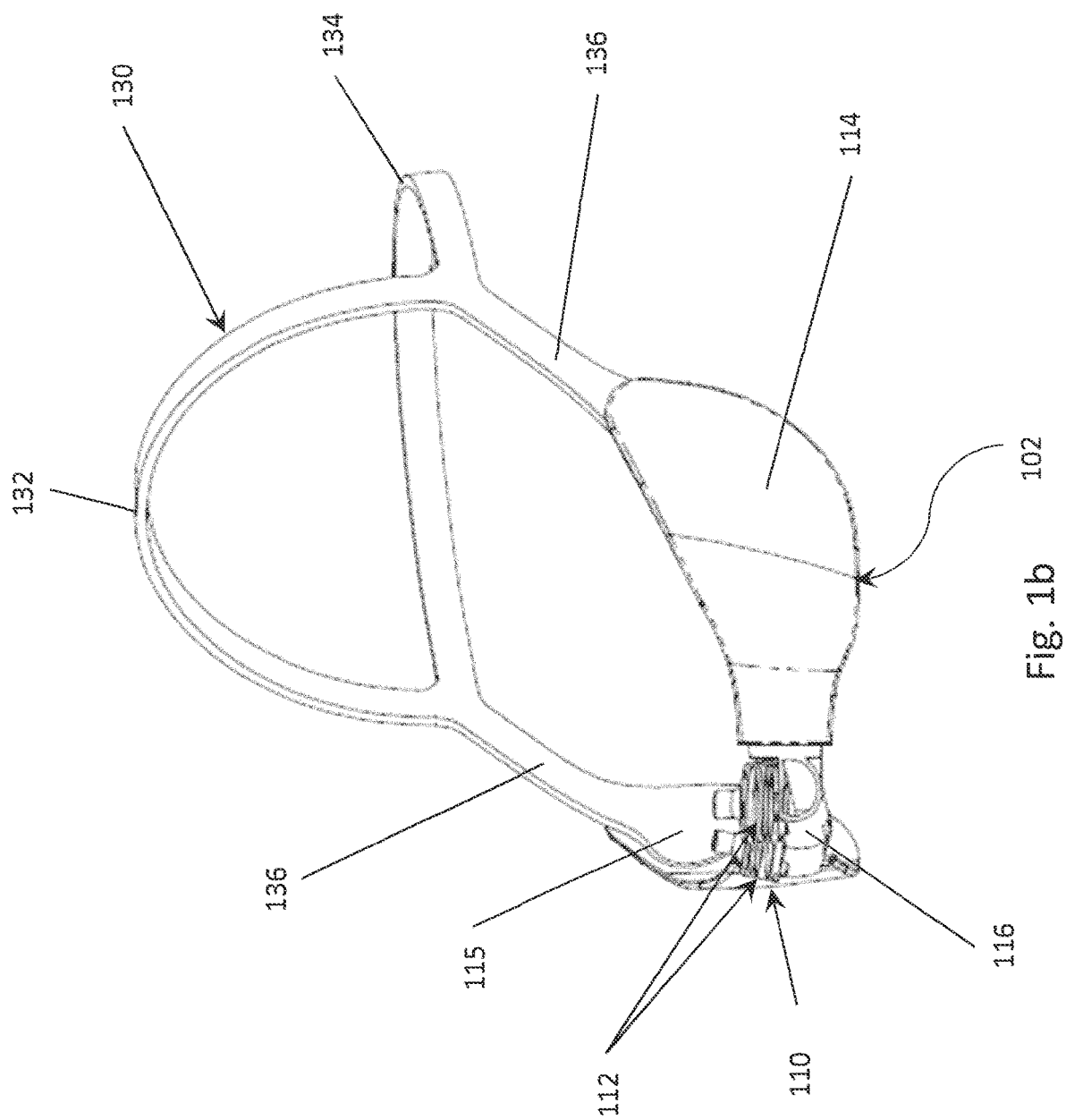
FIG. 1b is a perspective view of the respiratory mask of the present disclosure.

FIGS. 1a and 1b show a non-limiting exemplary embodiment of a respiratory mask system comprising a frame 102, headgear, tube 104, and sealing arrangement 110.

Frame:

In a non-limiting exemplary embodiment the frame 102 is configured to support and stabilize the sealing arrangement 110 against a patient's face. The sealing arrangement 110 comprises a pair of nasal prongs 112 that are configured to form a seal with the nares of the patient. The frame 102 comprises a pair of cheek supports 114 that are integrally formed with and spaced apart by a bridge portion 116. In use, the cheek supports 114 extend outwardly from the bridge portion 116, which extends from side to side below a patient's nose, and rearwardly across the cheeks and towards the ears. The cheek supports 114 are configured to engage the non-boney regions of the patient's cheeks below the zygomatic bone and form a brace that supports the bridge portion 116 relative to the patient's face.

Figure 2:
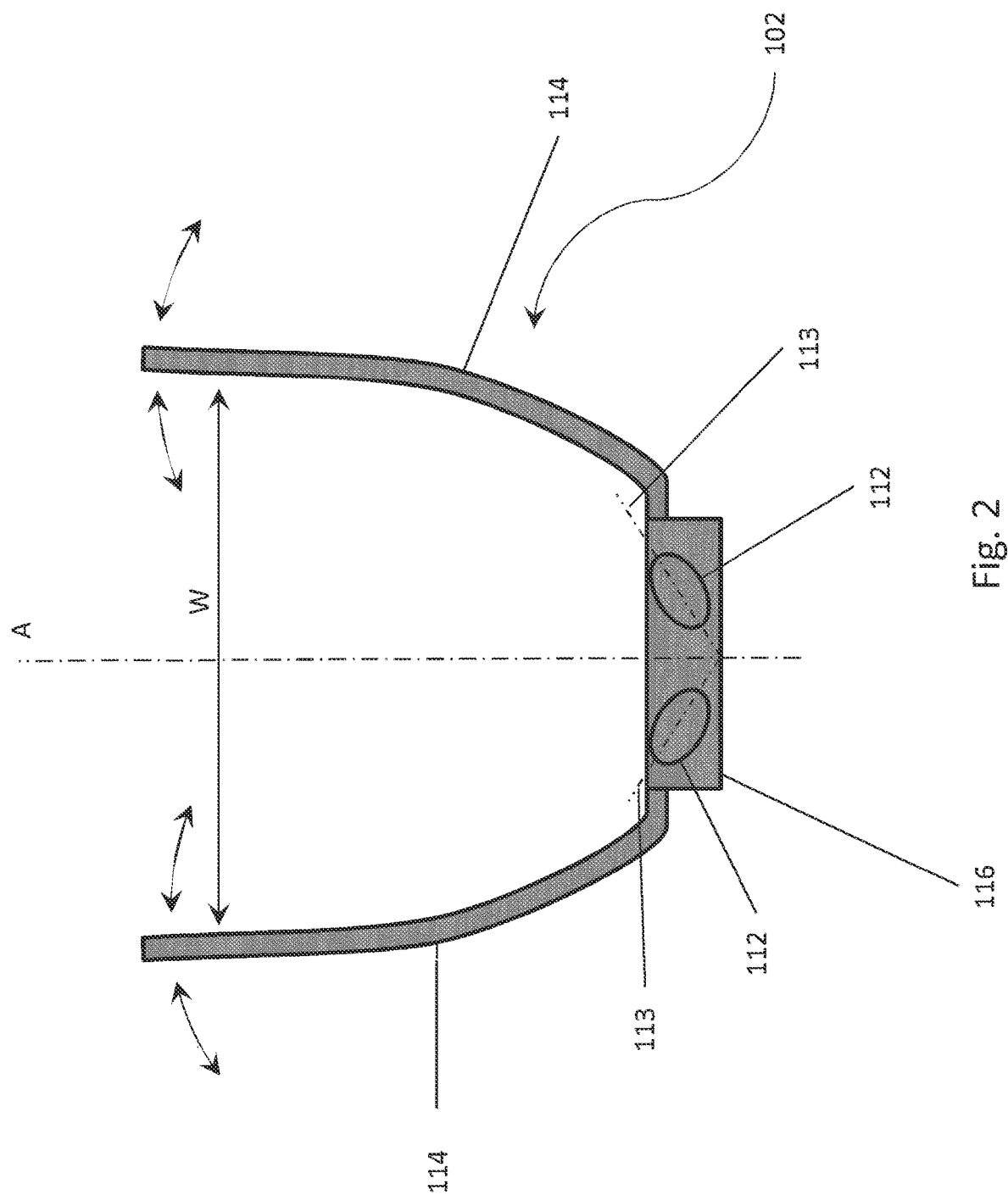
FIG. 2 is a schematic plan view of the frame of the respiratory mask of the present disclosure.

When viewed from above, as shown in FIG. 2, the frame 102 has a substantially 'U' shaped profile. The frame 102 is symmetrical about a central plane A In a neutral position, when the mask is not being worn by a patient, the cheek supports 114 can be spaced apart by a width W that is narrower than the width of most adult faces. This spacing provides a positive engagement between the patient's face and the frame 102. The frame 102 is made of a semi-rigid material that allows the cheek supports 114 to flex laterally (as shown by the curved arrows in FIG. 2) such that the width W is adjustable to cater for patients with different facial widths. This flex allows the frame 102 to apply a low level of force to the patient's cheeks and be partially self-supporting on the face without a headgear. Materials such as but not limited to polycarbonate, co-polyesters or nylon may be suitable for the frame 102. The semi-rigid material provides structure to the frame 102 that minimizes rotation and sideways movement of the sealing arrangement 110 that may cause leaks. The cheek supports 114 are able to flex independently of one another and the bridge portion 116. This allows one cheek support 114 to flex towards or away from a patient's face whilst the other cheek support 114 maintains the position of the bridge portion 116, and thus the sealing arrangement 110, relative to the patient's nose.

In some embodiments (not shown) the cheek supports 114 may comprise a core and a covering, wherein the core is made of the semi-rigid material as described, in relation to the frame 102, above and the covering comprises a fabric, silicone or other soft material. The semi-rigid plastics listed above may look and feel hard and or sharp, which may make the frame 102 undesirable for handling or positioning against the face of a patient. The covering is configured to provide a comfort layer between the semi-rigid core and the patient's face, and may also provide improved aesthetics to the frame 102.

The cheek supports 114 have a large surface area intended to inhibit the formation of pressure points on the patient's face, by spreading any load over a large area. The area is sufficient to reduce the skin loading to less than 20 mmHg, wherein 20 mmHg is the pressure at which damage to capillary vessels in the skin begins to occur. This is beneficial for patient comfort and the prevention of pressure sores. In one non-limiting exemplary embodiment the cheek supports 114 can have a combined surface area of at least 750 mm2. This surface area is sufficient to distribute a force of 2N such that the pressure on the face is less than 20 mmHg. In other embodiments the cheek supports 114 may have a combined surface area of about 3000 mm2. In another non-limiting embodiment the cheek support 114 has dimensions of approximately 75 mm by 40 mm.

The cheek supports 114 have an asymmetric profile with an upper edge that is configured to follow the line of a patient's cheek bone, and a lower edge that somewhat follows the line of the patient's jaw bone. The cheek supports 114 are curved such that they contact the patient's cheeks substantially evenly across the entirety of the surface area. This provides an even distribution of loads across the patient's cheeks. Being closely matched to the geometry of a patient's cheeks provides the cheek supports 114 with stability on the face, which in turn stabilizes the sealing arrangement 110 relative to the patient's nose.

Figure 3:
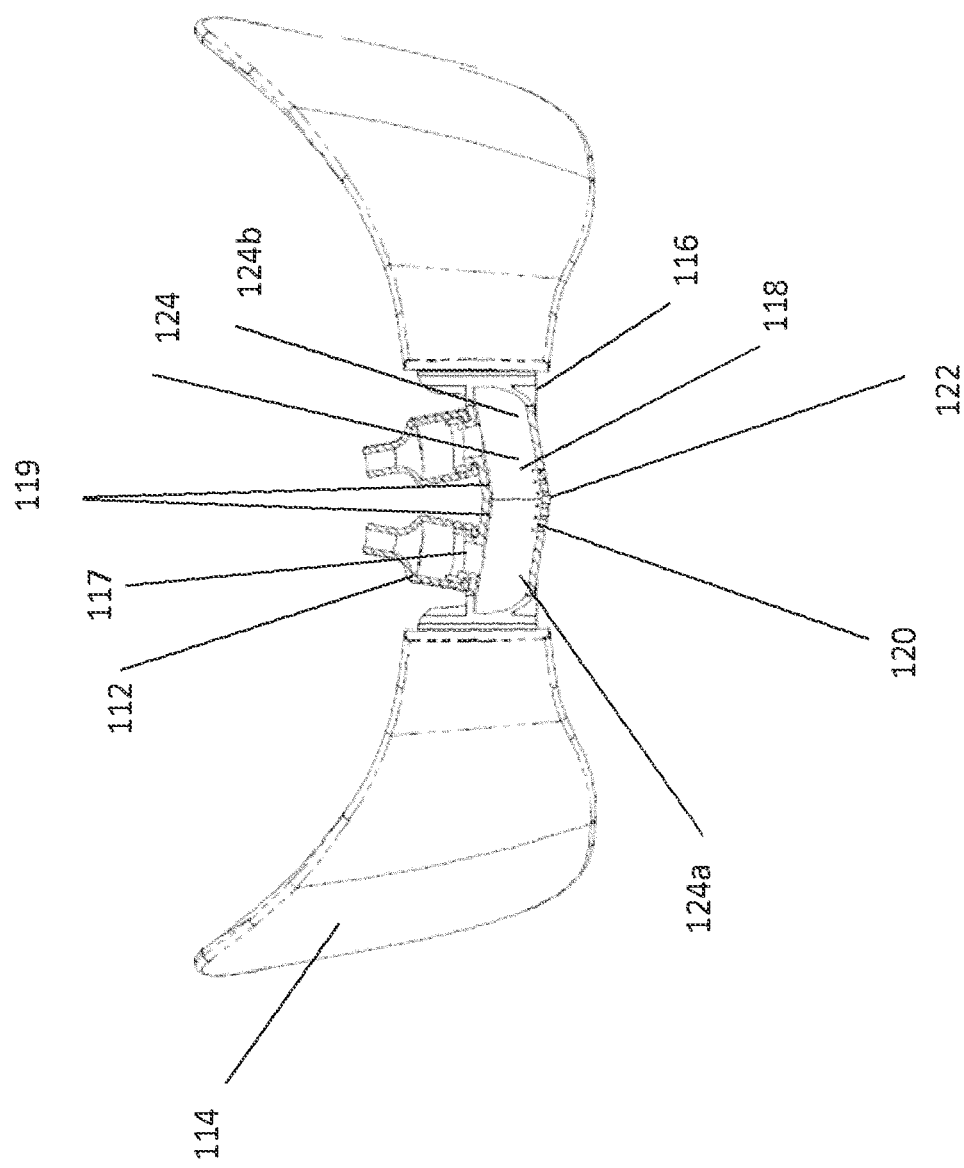
FIG. 3 is a cross-section front view of the frame and sealing arrangement of the presently disclosed respiratory mask.

As shown in FIG. 3 the bridge portion 116 comprises a plenum chamber 118 in the form of an elongate tube 124 that extends between the cheek supports 114 and has a central corner 122. The central corner 122 divides the elongate tube 124 into a first side 124a and a second side 124b. Each side of the elongate tube 124 has a semi-circular cross-sectional profile (as shown in FIGS. 1a and 1b), wherein a straight edge forms a flat surface 119 which is configured to receive the sealing arrangement 110. The central corner 122 is such that an obtuse angle is formed between the flat surfaces 119 of the elongate tube 124. This results in the nasal prongs 112 of the sealing arrangement 110 being angled towards each other and engaging more effectively with the nares of the patient.

The plenum chamber 118 is open at both ends and comprises a pair of spigots 117 and a bias flow vent 120. The plenum chamber 118 is configured to receive a flow of pressurized air through either of the open ends and be blocked at the opposing open end. The spigots 117 are positioned such that there is one on the flat surface 119 of each side of the elongate tube 124. They are configured to receive and retain the nasal prongs 112 and provide an air flow path between the plenum chamber 118 and the prongs.

The bias flow vent 120 comprises a plurality of holes positioned in the wall of the plenum chamber 118, opposing the spigots 117, configured to flush exhaled $CO_2$ from within the plenum chamber 118. The plurality of holes can be formed in the plenum chamber wall by means such as but not limited to laser drilling. Laser drilling the holes allows them to be aligned radially on the semi-circular wall of the plenum chamber 118, which will diffuse the air flow through the holes thus reducing noise and/or draft. The location of the bias flow vent 120 directs any draft, caused by the exhausted air, down and away from the patient, which may improve comfort for both the patient and their bed partner.

The bridge portion 116 is configured to support the sealing arrangement 110 at a substantially constant distance from the patient's face, and is positioned beneath the underside of a patient's nose extending across the upper lip. The cheek supports 114 are configured to support the bridge portion 116 at the substantially constant distance from the face. Preferably the bridge portion 116 does not contact or apply a pressure to the patient's upper lip, thus providing improved comfort. In an alternative embodiment the bridge portion 116 may contact the patient's lip whilst applying only a minimal pressure.

Figure 4:
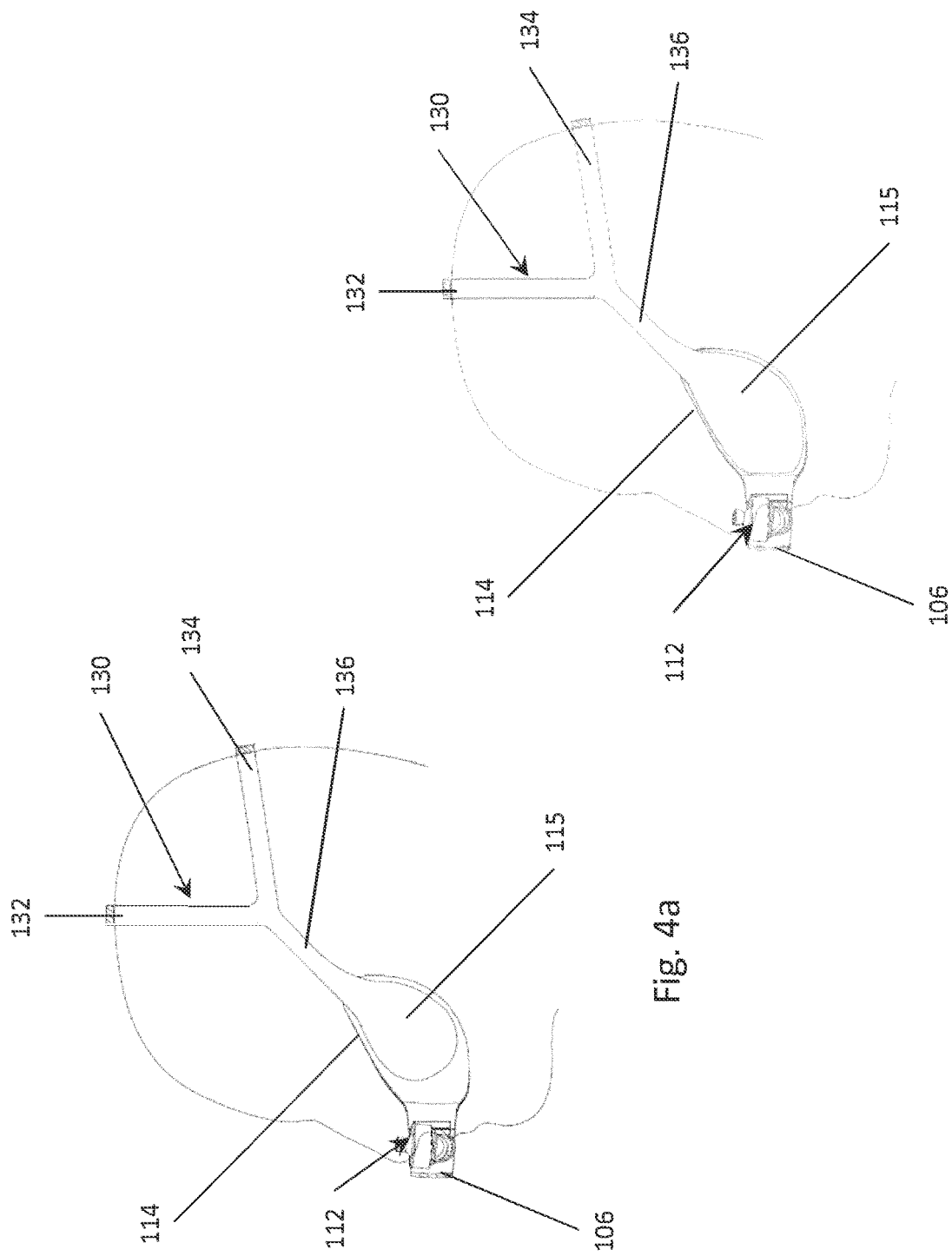
FIG. 4a and FIG. 4b are cross-sectional side views or two variations of the respiratory mask of the present disclosure.

Headgear:

The frame 102 is secured to a patient's head by a headgear system 130. FIGS. 4a and 4b show a non-limiting exemplary embodiment of the headgear 130. The headgear system 130 comprises a bifurcated configuration having a crown strap 132 and rear strap 134 that extend between the ends of two side straps 136. The side straps 136 are removably attached to the cheek supports 114 of the frame 102 and are configured to extend between the cheek supports 114 and the patient's face to provide a cheek pad 115 for comfort. The cheek pad 115 can be configured to cover a portion of the cheek support 114 (as in FIG. 4a) or the entirety of it (as in FIG. 4b). The larger the cheek pad the less likely it is that the patient will feel the hard plastic of the cheek supports 114. The cheek pads 115 can be repeatedly connected and disconnected to the cheek supports 114 by means, such as but not limited to, a hook and loop material (e.g. Velcro) or an adhesive surface.

The headgear system 130 can be made of any soft and flexible material, such as but not limited to a knit or woven fabric or a laminated material such as but not limited to Neoprene. Alternatively the headgear system 130 can be made of moulded plastic with an integrally formed fabric covering as described in U.S. Application U.S. 62/050,925, which is incorporated by reference herein in its entirety. In a non-limiting exemplary embodiment at least a portion of the headgear 130 may be elasticated to accommodate different head sizes and aid in the donning and doffing process. An elastic portion can aid in the fitting process by allowing the headgear system 130 to be stretched to a larger size when being pulled over the patient's head, which provides greater clearance. In an alternative embodiment the headgear system 130 can be substantially inelastic and there can be adjustment mechanisms incorporated into the straps to adjust their lengths either automatically or manually. Manual adjustment mechanisms can include, but are not limited to, buckles, buttons and hook and loop fasteners. An exemplary embodiment of an automatic adjustment mechanism is described in PCT application WO 2014/175752, which is herein incorporated by reference in its entirety. An inelastic headgear system 130 may be beneficial as it cannot increase the forces applied to a patient's head via and elastic return force.

Figure 5:
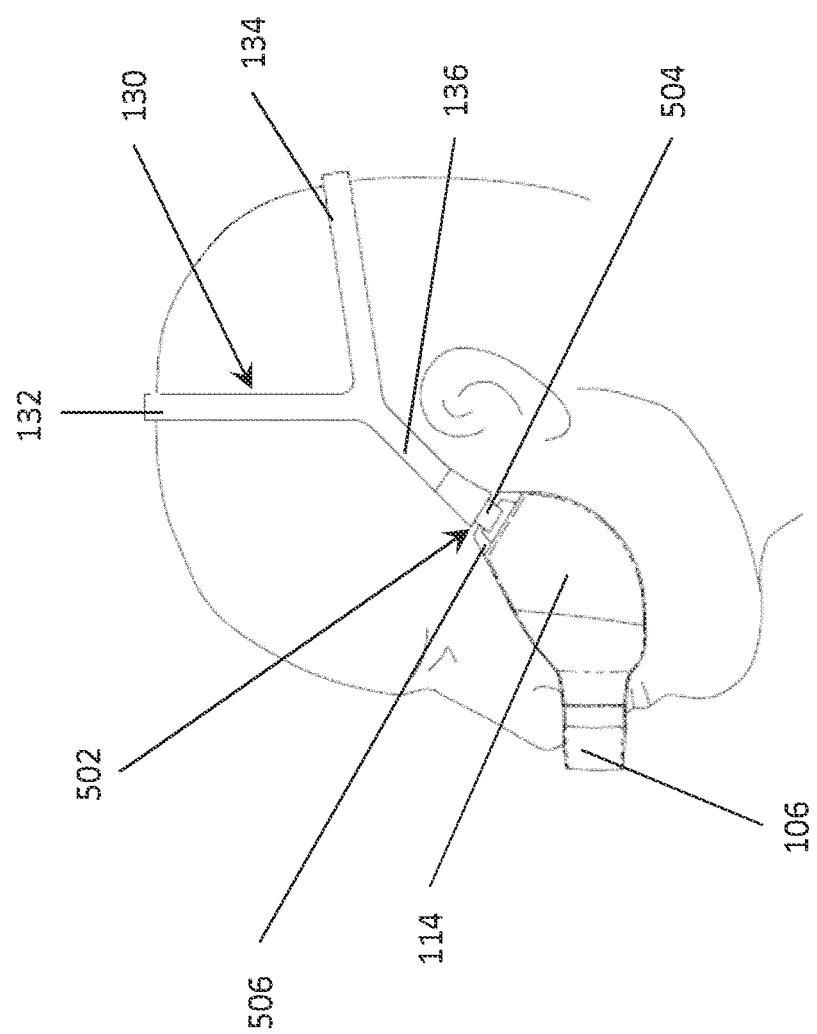
FIG. 5 is a side view of yet another variation of the respiratory mask of the present disclosure.

In an alternative non-limiting exemplary embodiment, shown in FIG. 5, the headgear system 130 does not include cheek pads 115 and connects to the cheek supports 114 by a clip mechanism 502. The clip mechanism 502 includes a hook portion 504 that is attached to the headgear system 130 and configured to connect to a post that forms part of a corresponding loop portion 506 that is located on the cheek support 114. In this embodiment cheek pads 115 can be provided to the cheek supports 114 as a separate component, or the cheek supports 114 can be configured to have a soft touch surface that is comfortable in direct contact with the patient's face.

The respiratory mask system of the present disclosure requires an air supply tube 104 to provide a connection between a supply of pressurized air and the plenum chamber 118 of the frame 102. The air supply tube 104 has two open ends wherein one end is configured to be connected to one of the open ends of the plenum chamber 118 and the other end is configured to be connected to the supply of pressurized air.

Figure 6B:
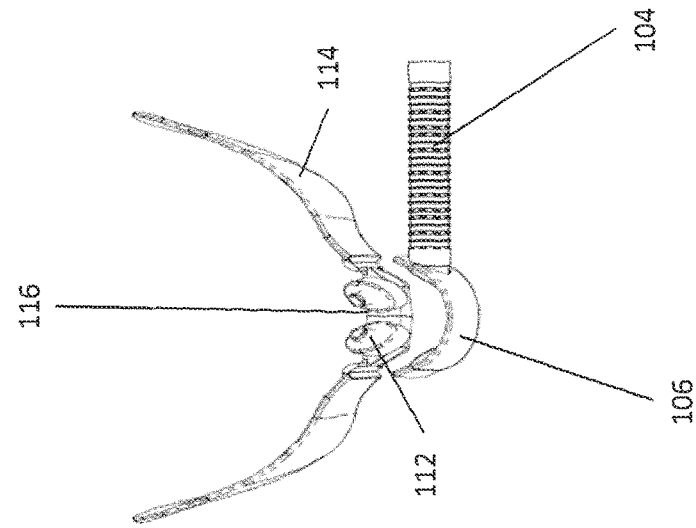
FIG. 6a and FIG. 6b are exploded perspective views of the respiratory mask of the present disclosure, with a tube housing in different orientations.
Figure 6A:
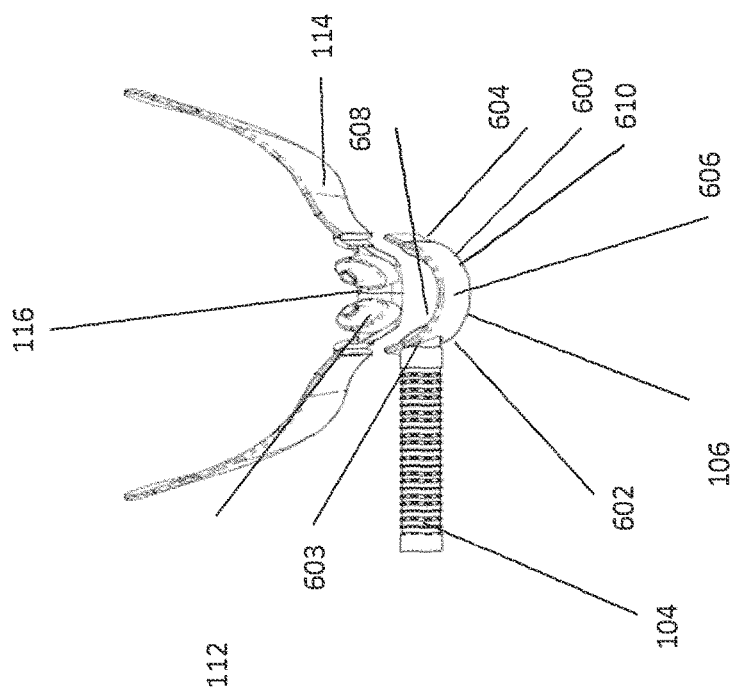
Figure 7:
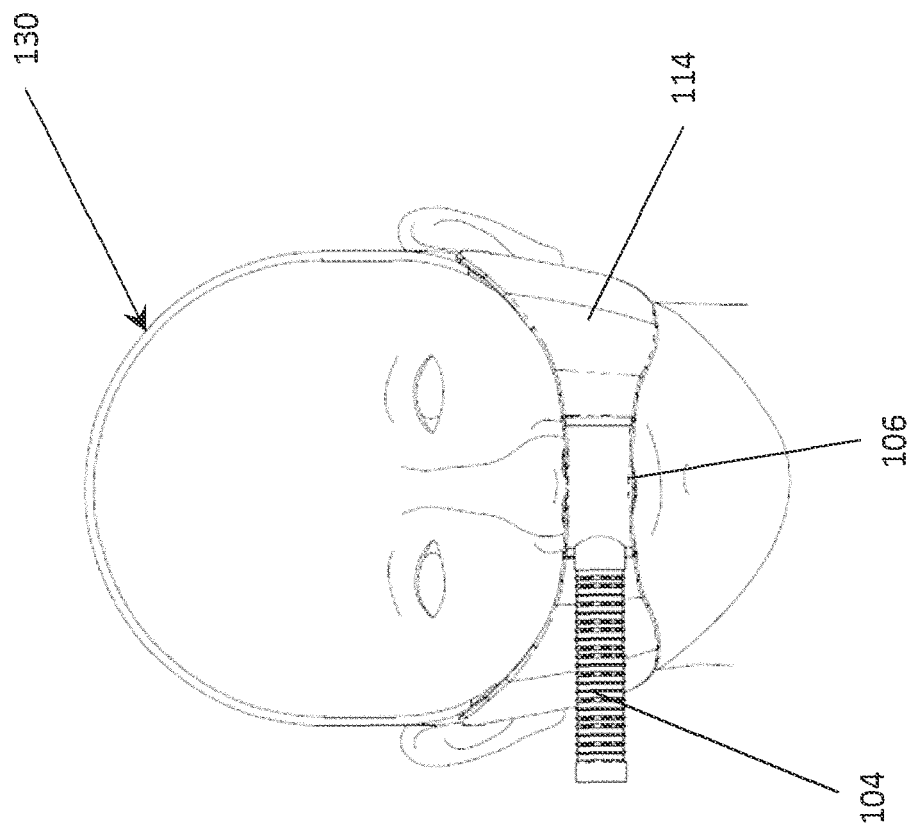
FIG. 7 is a front view of the respiratory mask of the present disclosure with the tube housing attached.

FIGS. 6a and 6b show a non-limiting exemplary embodiment of a tube housing 106 that is configured to secure the air supply tube 104 to the plenum chamber 118. The tube housing 106 comprises a semi-circular bracket 600 which has a first end 602 and second end 604 and a middle portion 606 that form internal side 608 and external side 610. The first end 602 has an opening 603 that extends through the housing 106 from the external side 610 to the internal side 608. The opening 603 is configured to receive the air supply tube 104 on the external side 610 and includes geometry configured to retain the tube 104 in place. The internal side 608 of the opening 603 is configured to sealingly engage with the first open end of the plenum chamber 118. The second end 604 has geometry that forms a bung (not shown) on the internal side 608. The bung is configured to enclose and/or seal the second open end of the plenum chamber 118, forming a closed air flow path between the air supply tube 104 and the sealing arrangement 110. The middle portion 606 forms a linking member between the opening 603 and the bung, and a cover that hides the bridge portion 116 and provides an aesthetically appealing appearance as shown in FIG. 7.

The tube housing 106 can be made of rubber, TPE or any other material that is resiliently flexible. This allows the tube housing 106 to be deformed to allow assembly to the bridge portion 116. The resiliently flexible material also forms an airtight bung that grips and seals the open ended plenum chamber 118. The shape of the tube housing 106 is substantially symmetrical (other than the tube opening and bung geometry) such that flipping the tube housing 106 over allows the air supply tube 104 to be attached to both ends of the plenum chamber 118, as can be seen in FIGS. 6a and 6b. This allows the patient to decide which side of the mask they want the air supply tube 104 to extend from and thus which side to sleep. Side entry of the air supply tube 104 may allow the wearer of the mask to sleep on their stomach as it doesn't extend as far in front of the face as a front entry which may be more obtrusive.

The tube housing 106 combines the bung and air supply tube 104 connection in a single component, which minimizes the total number of components in the mask. Having fewer components in the mask makes assembly of the mask less complicated and improves the ease of use for the patient by reducing the number of components that require cleaning and assembly.

In some configurations the tube housing 106 can act as a shield to the bias flow vent 120. It may direct the draft from the bias flow vent 120 in a downwards direction away from a potential bed partner. In an alternative embodiment (not shown) the bias flow vent 120 in the plenum chamber 118 may comprise a single opening that is configured to connect directly to the tube housing 106, which provides a venting configuration that includes a plurality of holes or any other appropriate diffusing means. In this configuration the tube housing 106 can include geometry on the internal side that is configured to form an air-tight seal with the single opening on the plenum chamber 118.

Nasal Prongs:

As shown in FIGS. 1a and 1b the sealing arrangement 110 comprises a pair of nasal prongs 112, configured to sealingly engage with the nares of the patient. The nasal prongs 112 are removably connected to and supported by the bridge portion 116 at a substantially constant distance from the patient's face.

FIGS. 8a to 8d show first and second non-limiting exemplary embodiments of a nasal prong 112, in compressed and uncompressed states. Both embodiments of the nasal prong 112 comprise a main body 800 having first and second ends, a sealing surface 802 and an outlet 804. The main body 800 comprises an elongate tube 124, wherein a wall structure 1006 is formed by a constant-force spring 810 covered or encased within a thin skin 808 of resilient and/or flexible material, such as but not limited to silicone. In some embodiments the spring 810 can have an elliptical profile, which will provide an elliptical sealing surface 802 that substantially matches the shape of a patient's nares. The elliptical profile of the nasal prongs 112 has a major axis 113 as shown in FIG. 2, wherein the major axes converge away from the patient in use. The thin skin 808 provides a membrane that links each of the spring coils together, forming a partially enclosed chamber within the spring 810. The thin skin 808 is configured to be highly flexible so as to have little or no impact on the compressibility of the spring

810. In some embodiments the thin skin 808 may resist elongation of the spring 810. In some embodiments the thin skin 808 may be inelastic in order to resist inflation due to the application of pressurized air to the nasal prongs 112.

The first end of the main body 800 is configured to form an air-tight connection with the spigots 117 of the bridge portion 116 (as shown in FIG. 3). The first end may in some embodiments include a keying feature (not shown) that indicates the orientation required to assemble the nasal prongs 112 to the bridge portion 116. The second end transitions into the sealing surface 802, wherein the thin skin 808 extends to form the sealing surface 802. The sealing surface 802 extends radially inwards from the wall structure 1006 of the main body 800 at an obtuse angle. In some embodiments the sealing surface 802 may include curved geometry that is configured to follow the facial geometry of a patient. The sealing surface 802 is configured to engage with the lower nasal surfaces and nares of the patient. In some embodiments the sealing surface 802 may be thicker than the thin skin 808. This may provide the sealing surface 802 with a resilient structure, which substantially maintains its shape when engaged with the nares of the patient.

The outlet is centrally located within the sealing surface 808. The outlet 804 provides a path through which the pressurized air passes from the nasal prong 112 to the air path of the patient. The outlet 804 has a smaller cross-sectional area than the main body 800 of the prong 112 and is configured to substantially match the internal size of a patient's nares.

Figure 8:
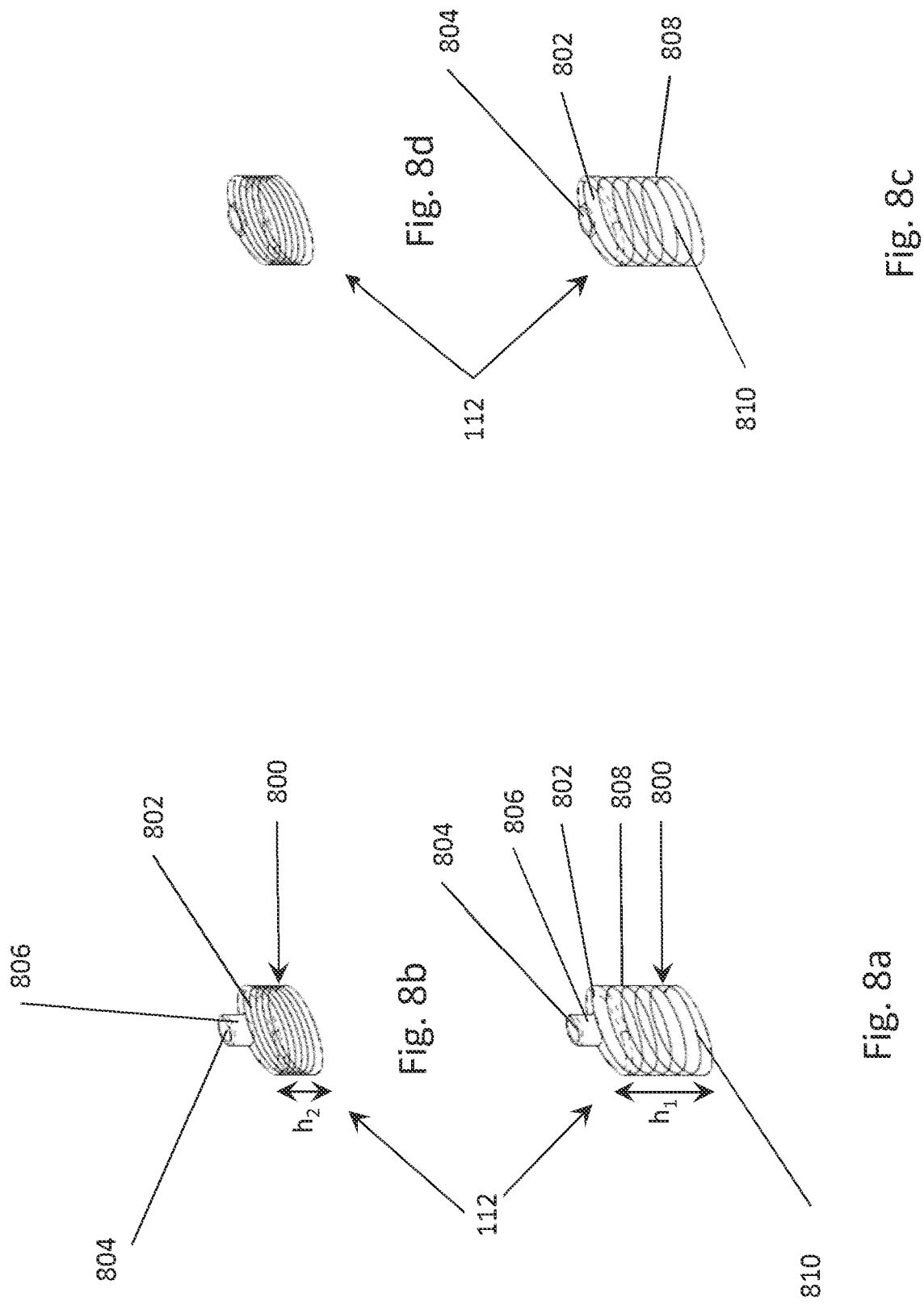
FIG. 8a, FIG. 8b, FIG. 8c and FIG. 8d are perspective views of two nasal prong embodiments in compressed and uncompressed states.

In the embodiment of FIGS. 8a and 8b the outlet 804 comprises a nozzle 806 that extends from the sealing surface 802 in a direction away from the main body 800. The nozzle 806 comprises a cylindrical portion that, in use, extends inside the nares of the patient. The cross-section of the nozzle 806 may be circular or elliptical. The nozzle 806 may help the patient to align the prongs 112 within their nares, and may help to prevent the prongs 112 from flicking out of the nares during use. In the embodiment of FIGS. 8c and 8d the outlet 804 comprises a centrally located orifice in the sealing surface 802. In some variations the outlet 804 may include a raised lip that extends around the perimeter of the orifice.

The main body 800 has an uncompressed height h1 that is greater than the distance between the bridge portion 116 and the nares or lower nasal surfaces of the user, in use. This height results in the nasal prong 112 undergoing an initial displacement and being compressed when the respiratory mask is donned by the patient. This compression allows the nasal prongs 112 to apply a substantially constant force against the nares of the patient, in use. The extent to which the spring is compressed is dependent on facial geometry of the patient and how far off the face the bridge portion 116 is supported. When compressed the nasal prong 112 has a height h2. The difference in height between h1 and h2 is the displacement range 900 of the nasal prongs 112.

The inclusion of a spring 810 within the prong 112 provides stability and resilience to the seal between the prong and the patient's nares. The spring 810 compensates for movement of the frame 102 or patient and allows the sealing surface 802 to remain in contact with the patient's nares. The spring 810 helps to isolate the sealing surface 802 from forces applied to other parts of the respiratory mask system. As such the sealing force 902 that is applied by the nasal prongs 112 to the nares of the patient is supplied predominantly by the spring.

Direct nasal respiratory masks utilize nasal prongs 112 (or pillows) having a sealing surface 802 that applies a sealing force 902 to the nares and/or lower nasal surface of a patient. The force applied to the nares and/or lower nose is a function of therapy pressure and headgear tension. If the sealing forces 902 are higher than necessary it can be uncomfortable for the patient and in some cases cause damage (necrosis) to their skin, therefore it is desirable to apply no more force than necessary.

Respiratory therapies require the application of a therapy pressure, in the form of a pressurized source of air, to the patient's airways via the respiratory mask. Therapy pressure results in a blow-off force 908 that is applied to the patient's face and pushes the respiratory mask away from the patient's face. The blow-off force 908 is a function of sealing surface area and therapy pressure. Tension forces in the headgear 130 increase to resist the blow-off force and avoid leaks occurring as a result of the mask lifting off the patient's face. The higher the therapy pressure the higher the blow-off force, and thus the higher the force applied by the headgear 130 to the patient's face and/or nares.

Headgear 130 is generally configured to secure the frame 102 and sealing arrangement 110 to the patient's face. In some applications the headgear 130 applies a force to their face and/or nares, even before the therapy pressure is applied. If the respiratory mask feels insecure on the patient's face or leaks are experienced between the sealing surface and their face, a typical course of action is to tighten the headgear 130. During adjustment of the headgear, it is possible for the headgear 130 to be over tightened. Over tightening of the headgear 130 can result in excessive force (i.e. a force greater than required for sealing) being applied to the patient's face and nares and thus discomfort. The forces applied by over tightened headgear 130 can be significantly higher than the force required for resisting the blow-off force 908, even at the highest therapy pressures.

The sealing force 902 applied to a patient's nares and/or lower nasal surfaces may be minimized by reducing therapy pressure and/or headgear tension. In practice therapy pressure cannot be selectively reduced to influence sealing forces. This is because each individual patient is prescribed a therapy pressure based on the severity of their condition, and this pressure needs to be maintained for the efficacy of the therapy. Therapy pressures typically range between 4 cmH20 and 20 cmH20. Since the therapy pressure cannot be adjusted to minimize forces on the nares, other means of reducing the force applied to the patient's nares are sought.

It may be possible to minimize the force applied to a patient's nares by reducing the ability of the patient (or clinician) to over tighten the headgear. This may be achieved by providing headgear 130 that is a fixed size. This is impractical as it would mean headgear 130 would need to be provided in a large number of sizes to fit the differing head circumferences of patients.

According to the presently disclosed subject matter, it is possible to minimize or predictably control the ability of the frame 102 and/or sealing arrangement 110 to transfer headgear forces to the patient's face. In a non-limiting exemplary embodiment a nasal prong 112 comprises a substantially constant force spring with a thin skin of flexible and/or resilient material. In use the nasal prong 112 is configured to act as a compensation system. As a result, in use, the nasal prongs 112 may be positioned at different proximities to the nares without affecting, or at least minimally changing, the force applied to the nares, yet still providing the necessary sealing forces.

Two non-limiting exemplary embodiments such as this are shown in FIGS. 8a to 8d. In such configurations, tightening the headgear 130 results in the spring 810 being compressed (displaced) before the tension forces of the headgear 130 are applied to the patient's face. Tightening the headgear 130 will not significantly increase the force applied to the nares until the spring 810 is completely compressed.

In another non-limiting exemplary embodiment the nasal prongs 112 may be used in combination with a headgear 130 having a fixed size that is larger than a patient's head circumference. In this configuration the compressibility of the spring 810 of the nasal prong 112 compensates for the difference between headgear size and head circumference, accommodating variation in patient head sizes; i.e. the springs 810 will be more compressed for patients with large head circumferences than for patients with small head circumferences. The displacement range 900 of the spring can be such that a small number of headgear sizes will cater for the majority of the population.

The nasal prong 112 is configured to provide a sealing force 902 upon an initial displacement of the spring, during fitment of the mask. This is so that the sealing surface 802 of the prong 112 is positively engaged with the nares of the patient and provides a sealing force 902 that prevents leaks. Additional displacement, within a displacement range 900, does not increase, or at least only minimally increases, force applied to the nares. In this regard, the required sealing force 902 is provided, but with minimal force applied to the patient's face and/or nares, even at a therapy pressure of 20 cmH20. Leaks are prevented at the highest possible blow-off force 908 and the lowest practical compression (displacement).

In some configurations the displacement range 900 of the spring 810 may assist in donning and doffing of the respiratory mask system. It can be beneficial for a respiratory mask headgear to have some elasticity or adjustability such that the circumference of the headgear and mask system can be enlarged during donning and doffing the mask. The enlargement in circumference provides clearance between the headgear 130 and the patient's head and allows the sealing arrangement 110 to be passed over the head with little resistance. According to the presently disclosed subject matter compression of the nasal prongs 112 provides clearance between the patients head and the headgear 130 that allows for easy donning and doffing of the respiratory mask.

In one non-limiting example the headgear 130 may be donned by the following method:
1. Locate the nasal prong in the nares of the patient
2. Apply a force to the mask such that the nasal prongs compress completely against the patient's nares,
3. Pull the headgear over the patient's head, with the nasal prongs compressed
4. Release the headgear and mask so that the nasal prongs expand and fill any space between the headgear and the patient's head.

Figure 9:
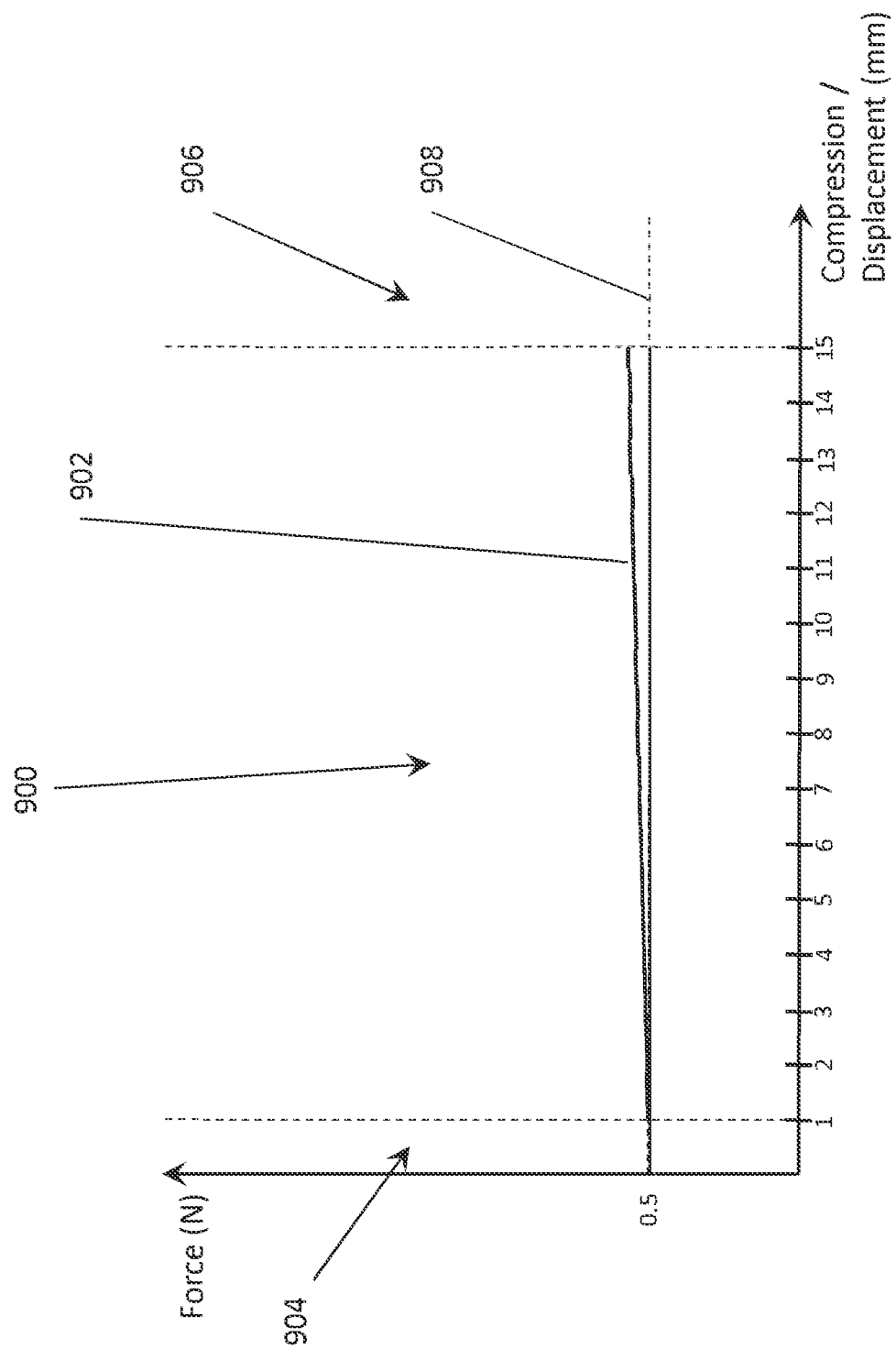
FIG. 9 is a force vs. displacement plot for the nasal prong of the present disclosure.

In a non-limiting exemplary embodiment the springs and the nasal prongs 112 are configured to be compressed by up to 15 mm. This displacement range 900 caters for differing facial geometries between patients, i.e. patients having a large nose or head circumference may require the nasal prong 112 to be compressed more than patients with small noses. The spring 810 is configured to apply a substantially constant sealing force 902 to the patient's nares, throughout the displacement range 900 of between about 1 mm and 15 mm as shown in the force vs displacement plot of FIG. 9. Outside of the displacement range 900 are two regions. The initial displacement region 904 is where the nasal prongs 112 are engaged with the patient's nares until the minimum sealing force 902 is applied. In alternative embodiments the displacement required to reach the minimum force may be less than 1 mm. The maximum compression region 906 is where the spring 810 reaches its maximum compression. In some embodiments the sealing force 902 may increase substantially once the spring 810 reaches maximum compression.

In a non-limiting example the contact area between the sealing surface of a pair of nasal prongs 112 and the nares of a patient can be about 270 mm2. For therapy pressures ranging from 5 to 20 cmH20, this contact area results in blow off forces between about 0.1N and 0.5N. Therefore the minimum spring force required for the nasal prong 112 to maintain an airtight seal is 0.5N. In order to avoid excessive forces being applied to the nares the spring 810 should have a low spring constant (or k value), such that the increase in force is small in comparison to the increase in compression (displacement).

Figure 10:
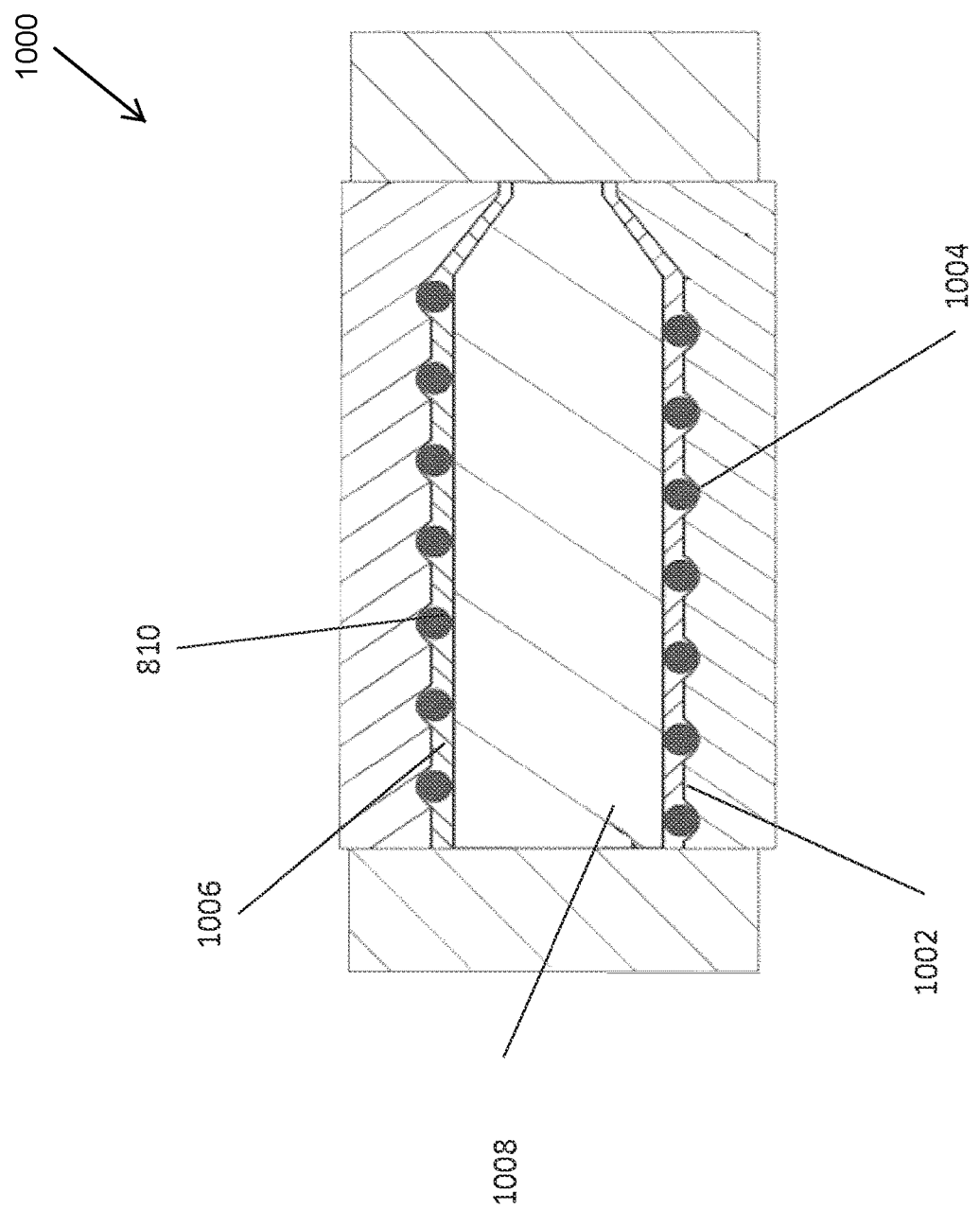
FIG. 10 is a schematic plan view of half of an injection mould tool that could be used to form the nasal prongs of FIGS. 8c and 8d.

The prongs can be formed by over-moulding silicone to a constant force spring 810. FIG. 10 shows a schematic view of half of a mould tool 1000 that could be used to form the nasal prongs 112. The mould tool 1000 includes a cavity 1002 with a helical recess 1004 that is configured to hold the spring 810 in place during injection of the silicone material that forms the walls structure of the nasal prongs 112. The recess prevents the spring 810 from being compressed by the pressure of the injected silicone. A core 1008 fits inside the spring 810, forms the internal surfaces and defines the wall thickness of the nasal prong 112.

In an alternative embodiment (not shown) the two nasal prongs 112 can be connected together and assembled to the bridge portion 116 as a single component. A configuration such as this reduces part numbers in the respiratory mask system and may prevent the loss of an individual nasal prong 112. In a first variation the two nasal prongs 112 can have a linking member that extends between them but does not form part of the air flow path. Each of the nasal prongs 112 is individually connected to the plenum chamber 118 of the bridge portion 116 but the linking member allows them to maintain a fixed orientation in relation to each other. In a second variation of this embodiment the nasal prongs 112 can be integrally formed as a single component with at least a portion of a plenum chamber 118 through which the pressurized air flow is supplied to the prongs. The prong and plenum chamber component can be attached to the bridge portion 116 which may or may not include a plenum chamber portion. In an embodiment where the plenum chamber 118 is formed entirely as part of the sealing arrangement 110 the bridge portion 116 will not be part of the air flow path. It will act as a support structure for the prong and plenum chamber component, and the tube, which connects directly to the prong and plenum chamber component.

What is claimed is:
1. A method for forming a nasal prong, the method comprising:
   positioning a spring within in a helical recess of a cavity of a mold tool;
   injecting a material into the mold tool to form a wall structure of the nasal prong between the mold tool and a core, the wall structure having an external surface formed at least partially by the helical recess, an internal surface formed by the core, and a thickness defined between the external surface and the internal surface;
   wherein the injecting the material into the mold tool forms a skin encasing the spring.

2. The method of claim 1, wherein the helical recess is configured to hold the spring in place during injection of the material.

3. The method of claim 1, wherein the helical recess is configured to prevent the spring from being compressed by a pressure exerted on the spring during injection of the material.

4. The method of claim 1, wherein the core is configured to define a wall thickness of the nasal prong.

5. The method of claim 1, wherein the core is disposed in a central portion the mold tool.

6. The method of claim 1, wherein the helical recess forms a portion of a surface of the cavity of the mold tool.

7. The method of claim 1, wherein the spring is a constant force spring.

8. The method of claim 1, wherein the material is a silicone material.

9. The method of claim 1, wherein the material is resilient and/or flexible.

10. The method of claim 1, wherein the spring comprises an elliptical profile.

11. The method of claim 1, wherein the skin is configured to provide a membrane that links each coil of the spring together, forming a partially enclosed chamber within the spring.

12. The method of claim 1, wherein the skin is configured to resist elongation of the spring.

13. The method of claim 1, wherein the skin is inelastic.

14. The method of claim 13, wherein the skin is configured to resist inflation due to an application of pressurized air to the nasal prong.

\* \* \* \* \*